United States Patent [19]

Schrier et al.

[11] Patent Number: 5,409,780
[45] Date of Patent: Apr. 25, 1995

[54] ANILINE ANALOGS FOR HYDROGEN PEROXIDE DETECTION

[75] Inventors: Wayne Schrier, Cupertino; Pawanjit S. Sethi, Livermore; Prithipal Singh, Los Altos, all of Calif.

[73] Assignee: Chemtrak, Inc., Sunnyvale, Calif.

[21] Appl. No.: 835,625

[22] Filed: Feb. 13, 1992

[51] Int. Cl.$^6$ ............................................. B32B 29/00
[52] U.S. Cl. ............................. 428/537.5; 428/411.1; 428/532; 428/537.7; 8/605
[58] Field of Search ................... 428/411.1, 532, 537.7, 428/537.5; 8/605

[56] References Cited

U.S. PATENT DOCUMENTS

| | | | |
|---|---|---|---|
| 4,973,549 | 11/1990 | Khanna et al. | 435/11 |
| 4,999,287 | 3/1991 | Allen et al. | 435/11 |
| 5,215,886 | 6/1993 | Patel et al. | 435/11 |

FOREIGN PATENT DOCUMENTS

| | | |
|---|---|---|
| 046969 | 3/1967 | Japan . |
| 123666 | 11/1984 | Japan . |
| 200170 | 3/1985 | Japan . |
| 034958 | 8/1985 | Japan . |

OTHER PUBLICATIONS

Hakano et al., "Spectrophotometric determination of hydrogen peroxide by the formation of indamine dye with catalyst of water-soluble iron porphyrin", Anal. Sci., 6(6), 823–6, pub. 1990.

Sawicki, et al. (1961) Anal. Chem. 33:722–725. Spot test detection and colorimetric determination of aromatic amines and imino heteroaromatic compounds with 3–methyl–2–benzothiazolone hydrazone.

Gochman and Scmitz (1972) Clin. Chem. 18:943–950. Application of a new peroxide indicator reaction to the specific, automated determination of glucose with glucose oxidase.

Ngo and Lenhoff (1980) Anal. Biochem. 105:389–397. A sensitive and veratile chromogenic assay for peroxidase and peroxidase-coupled reactions.

Geoghegan, W. (1985) Enzyme Mediated Immunoassays, Ngo and Lenhoff, eds. TX:Plenum:451–465. The Ngo-Lenhoff (MBTH-DMAB) peroxidase activity.

Wojciechowski (1990) Dyes and Pigments 12:273–286. Spectral peroperties of disperse dyes, derivatives of N-methylnaphthalimidoazobenzene.

Ando, et al. (1983) Anal. Biochem. 130:295–301. A sensitive spectrophotometric assay for guanase activity.

*Primary Examiner*—Paul J. Thibodeau
*Assistant Examiner*—David Abraham
*Attorney, Agent, or Firm*—Bertram I. Rowland

[57] ABSTRACT

Systems are provided for the detection of hydrogen peroxide for determination of analytes, where a N-alkylated 3-oxyaniline derivative is covalently bonded to a bibulous support and the other component for forming an indamine dye may be non-covalently bound to the support. Upon passage of a transport medium across the support in the presence of hydrogen peroxide and a peroxidase, an indamine dye is formed. Where a limited amount of hydrogen peroxide is introduced at a site proximal to one end of the support, and the hydrogen peroxide migrates toward the other end, the distance of color development will be related to the amount of hydrogen peroxide, which can be correlated to the amount of analyte in a sample.

11 Claims, No Drawings

ANILINE ANALOGS FOR HYDROGEN PEROXIDE DETECTION

TECHNICAL FIELD

The field of this invention concerns dye combinations for hydrogen peroxide detection.

BACKGROUND

There are a wide variety of applications, where the detection of hydrogen peroxide is associated with a determination of interest. The systems include histology, cytology, cell identification, and diagnostic assays. Diagnostic assays may be divided between those assays which occur in solution and those assays which are detected on a solid surface.

There has been substantial development in diagnostic assays occurring on a surface. In one embodiment, migration distance as detected by color development is used for the determination of an analyte. In this way, quantitative results can be obtained without the use of sophisticated equipment. By employing a graduated scale in association with a bibulous strip, the length of the region of color development can be directly read into a concentration for the analyte.

In these assays, the dye is produced by the reaction of two molecules, one bound to the solid surface and the other in solution. The reaction of a peroxidase with hydrogen peroxide results in oxidation of one of the two molecules, which then reacts with the other molecule to form the dye.

There are a number of variables of concern associated with such assays. The ease of reading the length of the region of color development is one important aspect, particularly that the line of demarcation between the region of color development and the region where color development is absent is fairly sharp. Secondly, the reproducibility of the assay is an important variable, as well as the standard deviation. Other considerations include the rate of reaction between the two molecules, the susceptibility to influences of components in the sample, storage stability, intensity of color development, and the like. There is, therefore, substantial interest in finding dye components which will optimize the assay results.

RELEVANT LITERATURE

Sawicki, et al., *Anal. Chem.* 33:722–725 (1961) describe the use of indamine dyes. Gochman and Schmitz, *Clin. Chem.* 18:943–950 (1972) describe a glucose determination using indamine dye. Ngo and Lenhoff, *Anal. Biochem.* 105:389–397 (1980) and W. Geoghegan, "The Ngo-Lenhoff (MBTH-DMAB) Peroxidase Assay", *Enzyme Mediated Immunoassays* T. T. Ngo and H. M. Lenhoff eds., Houston, Tex.:Plenum, 1985, pp. 451–465 describe assays for hydrogen peroxide. Wojciechowski, *Dyes and Pigments* 12:273–286 (1990) describes determination of N-methyl naphthalimidobenzene. Ando, et al., *Anal. Biochem.* 130:295–301 (1983) describe an assay for guanase activity using an indamine dye.

SUMMARY OF THE INVENTION

Functionalized N-alkyl 3-oxyanilines are employed as insoluble members of an indamine dye combination, bound to a bibulous solid surface, where the other member is dispersed in solution. The oxyanilines find use in assays, where hydrogen peroxide is associated with analyte concentration and in the presence of a peroxidase, the indamine dye is formed. The amount of analyte is related to the length of a region of color development, where the use of the subject oxyanilines provides for more accurate reproducible results.

DESCRIPTION OF THE SPECIFIC EMBODIMENTS

In accordance with the subject invention, combinations of precursors to indamine dyes are employed, where the aniline moiety is a functionalized N-alkyl 3-oxyaniline. The subject precursor combinations find particular use, where the oxyaniline component is bound to a bibulous surface, while the other component is dispersed in solution. The reaction to form the indamine dye is as a result of the reaction of a peroxidase with hydrogen peroxide or other peroxide.

The aniline compounds of this invention will normally have about 9 to 15 carbon atoms, more usually from about 9 to 12 carbon atoms, where the aniline nitrogen will be at least monoalkylated, where one of the groups will be a substituted alkyl group of from about 2 to 7, usually 2 to 5 carbon atoms and the other group will be hydrogen, alkyl or hydroxyalkyl, the alkyl usually being of 1 to 3 carbon atoms, more usually of 1 to 2 carbon atoms, where the hydroxyl group is separated from the nitrogen by at least 2 carbon atoms. The functional group may be terminal or non-terminal, depending upon the nature of the functional group, usually being separated by at least 2 carbon atoms from the aniline nitrogen.

The functional groups will allow for conjugation to the bibulous surface. Depending on the nature of the bibulous surface, and its functionalization with reactive groups, the functional groups may take many forms. The functional group may be amino, thio, oxy, active halo, pseudohalo, carboxy, cyano, aldehyde, etc. These groups are well known for coupling and will usually be coupled to carboxy groups, amino, activated olefin, active halo, etc. to provide for stable covalent coupling. Preferred functional groups are amino and carboxy.

The 3-oxy group will usually be hydroxy or alkoxy of from about 1 to 4, more usually 1 to 3 carbon atoms, where the alkyl group may be straight or branched.

The aromatic ring may be mono- or bi-, carbo- or heterocyclic, usually having not more than one heteroannular member, where the aniline amine will be at the peri position (adjacent to the fused carbon on the ring). The other ring will be carbocyclic or heterocyclic of from 5 to 6 annular members and having 0 to 1 heteroatom.

Other groups may also be present, particularly polar groups to enhance water solubility, such as carboxy, sulfonato, borate, normally ionizable groups.

Illustrative compounds include N-(5-aminopentyl-1) 3-ethoxyaniline; N-(4-aminobutyl-1), N-methyl 3-methoxyaniline, N-(4-aminobutyl-1), N-hydroxyethyl 3-ethoxyaniline; N-(5-aminopentyl-1), N-hydroxyethyl 3-hydroxyaniline; 4-(N-(3-carboxypropyl-1)) 6-methoxybenzofuran; 4-(N-(5-thiolpentyl-1), N-methyl) 6-ethoxybenzthiophene; N-(6-aminohexyl-1), N-hydroxyethyl 3-methoxyaniline. The compounds may include carboxy, sulfonato or other groups at available positions meta or para to the aniline nitrogen.

The other member of the indamine dye may be benzthiazolinone hydrazone, such as 3-methyl-2-benzothiazolinone hydrazine hydrochloride (MBTH).

The aniline compounds of this invention will for the most part have the following formula:

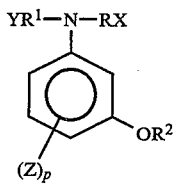

wherein:
R is an alkylene group, straight chain or branched, of from 2 to 6, usually 2 to 5 carbon atoms;
$R^1$ is a bond or an alkylene group of from 1 to 3 carbon atoms, usually 1 to 2 carbon atoms;
$R^2$ is hydrogen or an alkyl group of from 1 to 3, usually 1 to 2 carbon atoms;
p is 0 or 1;
Y is hydrogen or hydroxyl, when $R^1$ is alkylene, there being 2 carbon atoms between the hydroxyl and nitrogen to which $R^1$ is attached, and hydrogen when $R^1$ is a bond;
X is a functional group for covalent bonding to a bibulous support, including amino, carboxy, thio, activated olefin, cyano, aldehyde, active halo, pseudohalo, and the like;
Z is a polar functional group to impart water solubility to the compound, usually acidic, such as carboxy, sulfonate, or the like, generally having from 2 to 8 atoms and 0 to 1 carbon atom, other atoms being hydrogen or heteroatoms, such as oxygen, sulfur, nitrogen, boron, or the like;
with the proviso that the 5 and 6 positions may be joined by a 3 to 4 atom bridge to define a carbocyclic or heterocyclic fused ring having 1 heteroatom, which is N, O, or S.

The oxy substituent is normally meta.

The coupling compounds are used in solution, normally a buffered solution, comprising peroxidase and hydrogen peroxide, which will normally be present in low concentration, usually below about 100 nmoles/10 μl of sample e.g. serum. The hydrogen peroxide may be present as a result of addition of hydrogen peroxide or as a result of formation of hydrogen peroxide in situ. Particularly, hydrogen peroxide may be the result of a reaction between an oxidase and its substrate, such as cholesterol oxidase, glucose oxidase, uricase, and the like. The peroxidase which is present will normally be present at a concentration in the range of about 0.01 to 10 U/ml, more usually 0.1 to 5 U/ml. Usually, the medium will be buffered with a conventional buffer, such as phosphate, TRIS, MOPS, etc., at a pH in the range of about 6 to 8. The soluble coupling member will generally be present in total amount less than available aniline molecules, generally at a concentration of at least about 0.01 mg/mL and not more than about 1 mg/mL, preferably about 0.05 to 0.5 mg/mL.

The aniline derivatives may be readily conjugated to a bibulous support. The bibulous support may be paper, glass fibers, nitrocellulose, etc., or other bibulous support which allows transport of aqueous media and conjugation of the aniline derivative to the support. Conjugation with the functional group may be with a carbonyl functionality, either non-oxo or oxo-carbonyl, that is, carboxy, aldehydo or keto, cyano amino, active olefin, thio, etc., as previously described. For the most part, with the amino functionality, carboxy derivatives will be employed, which may be activated with carbodiimides, carbonyl diimidazole, activating hydroxyl compounds to form activated esters, such as dinitrophenol, pentachlorophenol, N-hydroxy succinimide, etc. The manner of activating carboxy substituted bibulous supports is well known in the literature, see, for example, Chapman and Ratcliffe, *Clin. Chem. Acta.* 118:129–134 (1982).

Various activated bibulous supports are available, which may be combined with the subject aniline compound in a polar medium, either organic, aqueous, or combination thereof, conveniently in the presence of an unreactive acid scavenger, e.g. tertiary-amine. The aniline concentration will generally be in the range of about 5 to 100 mM. The reaction may be carried out under ambient conditions, for sufficient time for the reaction to go to substantial completion. Substantial excess of the aniline derivative may be used, usually 2 or more fold excess, over active groups on the support. After completion of the reaction, the support may be thoroughly washed, conveniently with the reaction medium and may then be followed by a wash with mild acid, e.g. 0.01 to 0.02N $H^+$. The washes may be repeated until the absorbance reading is below about 0.01 at a wavelength at or approximately at the maximum absorbance wavelength.

Any remaining reactive moieties present on the support may then be blocked by adding an appropriately reactive compound, particularly an amino compound, such as hydroxylamine. After completion of the reaction, usually after at least about 0.5 h, and not more than about 6 h, the support may then be thoroughly washed to ensure the substantial removal of all unbound reagents. Upon completion of the washing, the supports may then be dried and stored in a dry box.

The other component of the indamine dye may be present in solution or may be non-covalently bound to the support. Depending upon the concentration of the aniline derivative, the solution of the other component may range from about 0.01 to 1 mg/mL, usually from about 0.05 to 0.5 mg/mL. Complete immersion of that portion of the strip to which the soluble component is to be bound is ensured and desirably the strip may be rotated one or more times in the solution to ensure uniform exposure of the support to the solution and the component in the solution. Approximately 1 mL of solution is used per 1 $cm^2$ square support.

The subject supports with a covalently bound aniline and non-covalently bound other component of the indamine dye couple may be used in a wide variety of assays for detecting hydrogen peroxide. They are particularly useful in assays where the hydrogen peroxide is introduced to the support proximal to one end of the support in the presence of a peroxidase and is transported by an aqueous medium toward the other end of the support, whereby the hydrogen peroxide becomes exhausted through reaction. Thus, the amount of hydrogen peroxide introduced to the support is less than the amount which will cause complete reaction of all of the aniline component bound to the surface. In this way, the distance from one end of the support to the border of color development is an indication of the amount of hydrogen peroxide present in the transport medium.

This technique may be used for a wide variety of assays, particularly assays where hydrogen peroxide is produced in relation to the amount of analyte in a sample. For example, many analytes may act as enzyme substrates with the production of hydrogen peroxide in the presence of air. These analytes include cholesterol, glucose, uric acid, etc. Alternatively, one may provide for antibodies to be covalently bound to the support surface as well as the aniline component. By providing for competition between the analyte and analyte (or other cross-reactive species) conjugated to peroxidase, by transport of the sample and conjugate beginning proximal to one end of the strip and migrating toward the other end, the distance of color development may be a measure of the amount of analyte in the sample. Other protocols may also find application.

The subject compounds have a number of advantages, individually or in combination, including improved storage stability, sharp differentiation at the border of reaction, and color formation, ease of handling, reactivity and the like. They also provide good separation with varying peroxide concentration and low standard deviation.

The following examples are offered by way of illustration and not by way of limitation.

EXPERIMENTAL

Materials

CDI activated Whatman 31-ET paper (lot P1005)
Substrates:
5-(N-methylaniline) pentanoyl ethylenediamine (N-MAD)
N-[ω-1,2-ethylenediamine carboxamidobutyl],
N-ethyl 3-methoxyaniline (3-methoxy N-MAD)
N-(2-aminoethyl) aniline
N-methyl, N-(4-aminobutyl) aniline
N-methyl, N-(2-aminoethyl) aniline
N-(2-hydroxyethyl), N-(2-aminoethyl) aniline
N-(4-aminobutyl) 3-methoxyaniline
N-(4-aminobutyl) 3-hydroxyaniline
Triethylamine
Acetonitrile
0.025M HCl
Hydroxylamine HCl
0.1M $Na_2HPO_4$, pH 7.0
3-methyl-2-benzothiazolinone hydrazone hydrochloride (MBTH)
Preciset cholesterol standards
Wicking buffer

Methods

Immobilization of Substrates. Each substrate was made up at 16 mM containing 32 mM triethylamine (a proton scavenger) in acetonitrile. CDI activated Whatman 31-ET paper was cut into strips approximately 28 cm×7 cm. Mesh screens were cut the same size. A mesh screen was placed on top of one strip of CDI paper and the two were rolled together and placed in a 50 mL conical centrifuge tube. The tube was covered with aluminum foil. Each tube was filled with a substrate solution and immobilized overnight with constant rotation. The substrate solution was discarded and the papers were washed with acetonitrile for 15 five minute washes with constant rotation. The papers then underwent five minute washes with 0.025M HCl. These washes were continued until an absorbance reading of 0.01 or less at 255 nm was obtained. The papers were then blocked by adding 50 mL of 0.25M hydroxylamine HCl in 0.1M $Na_2HPO_4$, pH 7.0 to the centrifuge tubes and rotated on a rotating disc for two hours. The hydroxylamine solution was removed and the papers were washed with 50 mL of deionized water which was changed every 15 minutes for a total of four washes. Each paper was then transferred to its own glass dish (approximately 8"×11") which was filled with approximately 400 mL of deionized water and washed for a total of five washes, changing the deionized water every five minutes. The papers were then dried at 80° C. for 25 minutes and stored in the dry box.

Loading of MBTH. The papers were next cut into approximately 7 cm squares. Each analog was dipped at both 0.1 and 0.3 mg/mL MBTH by placing 50 mL of MBTH solution in a glass dish (8"×11") which was tilted slightly at the upper end. One analog was dipped per 50 mL of solution by inserting one end in the liquid and pulling the paper through, then rotating the paper 90° and repeating the dipping process, followed by drying at 80° C. for 15 minutes.

Lamination of Substrate Papers. MBTH papers were laminated onto plastic cards which consisted of a 9 mm Whatman 31-ET wicking strip which overlapped a 5 mm Whatman 31-ET sample pad by 1 mm, followed by a 5 mm conversion pad (overlapping the sample pad by 1 mm) and aligned to a 70 mm substrate paper for a total card width of 9.5 cm. These cards were then cut into 5 mm wide strips. Note: The conversion pad contains stabilized cholesterol esterase and cholesterol oxidase.

Cholesterol Assay. Preciset ™ cholesterol standards were used to generate standard curves comparing migration height to cholesterol concentration. Five (5) μL of 100, 200 and 300 mg/dL Preciset cholesterol standards were added to the sample pad using strips containing the 0.3 mg/mL MBTH dipped papers. Five (5) μL of 50 mg/dL (to yield a 25 mg/dL sample) or 10 μL of 50 and 100 mg/dL Preciset cholesterol standards were added to the sample pad of the strips containing the 0.1 mg/mL MBTH dipped papers. The strips were then placed into 500 mL of wicking buffer which contains horseradish peroxidase. Each concentration of cholesterol was run in triplicate for each substrate paper. The migration heights were measured and the average and s.d. were determined.

TABLE 1

| 0.1 mg/mL MBTH | | | | |
|---|---|---|---|---|
| | | Migration Height (mm) +/− s.d. [Cholesterol] mg/dL | | |
| Substrate | Extinction Coefficient | 25 | 50 | 100 |
| 3-methoxy N-MAD | 95000 | 23.5 +/− 1.32 | 39.5 +/− 0.5 | 54.0 +/− 1.0 |
| N-MAD | 45000 | 21.8 +/− 0.76 | 38.5 +/− 2.29 | 56.3 +/− 0.29 |
| N-2-aminoethyl aniline | 76900 | 26.2 +/− 1.15 | 42.2 +/− 0.76 | 59.7 +/− 0.29 |
| N-methyl-N-4-aminobutyl aniline | 77200 | 25.5 +/− 0.5 | 41.7 +/− 1.53 | 57 +/− 3.61 |
| N-methyl-N-2-aminoethyl aniline | 74800 | 25.0 +/− 1.32 | 40.7 +/− 3.06 | 59.3 +/− 0.58 |
| 3-methoxy-N-4-aminobutyl aniline | 77000 | 21.0 +/− 0.87 | 35.2 +/− 0.76 | 48.8 +/− 2.57 |
| 3-hydroxy-N-4-aminobutyl | N/A | 21.3 +/− 0.29 | 33.8 +/− 1.53 | 51.7 +/− 1.53 |

TABLE 1-continued 0.1 mg/mL MBTH

| Substrate | Extinction Coefficient | Migration Height (mm) +/− s.d. [Cholesterol] mg/dL | | |
|---|---|---|---|---|
| | | 25 | 50 | 100 |
| aniline | | | | |

Table of substrates dipped at 0.1 mg/mL MBTH giving migration heights and s.d. at 25, 50 and 100 mg/dL cholesterol.

NOTE: While the extinction coefficient does not vary significantly with the length of the N-alkyl moiety, the color intensity on the paper is directly related to the chain length. The general observation is that as the chain length increases from 2 to 4 carbon units the intensity of the color of the peaks increases. We attribute the increase of color with the chain length to an as yet unidentified factor associated with formation of the indamine dye on the solid support.

TABLE 2

0.3 mg/mL MBTH

| Substrate | Extinction Coefficient | Migration Height (mm) +/− s.d. [Cholesterol] mg/dL | | |
|---|---|---|---|---|
| | | 100 | 200 | 300 |
| *3-methoxy N-MAD | 95000 | 16.2 +/− 0.29 | 27.7 +/− 1.15 | 31.8 +/− 0.29 |
| N-MAD | 45000 | 17.3 +/− 3.2 | 31.5 +/− 3.04 | 41.0 +/− 3.46 |
| N-2-aminoethyl aniline | 76900 | 19.5 +/− 1.8 | 31.5 +/− 1.32 | 41.5 +/− 0.87 |
| N-methyl-N-4-aminobutyl aniline | 77200 | 20.0 +/− 1.0 | 30.8 +/− 0.29 | 40.5 +/− 0.5 |
| N-methyl-N-2-aminoethyl aniline | 74800 | 18.5 +/− 1.0 | 33.0 +/− 1.0 | 44.5 +/− 0.5 |
| 3-methoxy-N-4-aminobutyl aniline | 77000 | 21.0 +/− 0.87 | 35.2 +/− 0.76 | 48.8 +/− 2.57 |
| 3-hydroxy-N-4-aminobutyl aniline | N/A | 21.3 +/− 0.29 | 33.8 +/− 1.53 | 51.7 +/− 1.53 |

*dipped at 0.25 mg/mL MBTH

Table of substrates dipped at 0.3 mg/mL MBTH giving migration heights and s.d. at 100, 200, and 300 mg/dL cholesterol.

It is evident from the above results, that the subject compounds provide for excellent sensitivity and response to variation and concentration of analytes, where the amount of analyte is related to the amount of hydrogen peroxide which is produced enzymatically. Low standard deviations are achieved and good spreads between the various concentrations. Thus, one can quantitatively determine the amount of analyte in a reproducible manner. In addition, the color which is produced is readily discernible at the border, which substantially enhances the accuracy in reading and reduces the subjectivity of the determination.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A bibulous strip comprising a 3-oxy substituted N-(functional group substituted alkyl) aniline covalently bonded to said strip through said functional group, said alkyl group of from 2 to 6 carbon atoms.

2. A bibulous strip according to claim 1, wherein said 3-oxy group is alkoxy of from 1 to 4 carbon atoms.

3. A bibulous strip according to claim 1, wherein said aniline is fused to a ring of from 5 to 6 annular members and up to one heteroannular member.

4. A bibulous strip according to claim 1, wherein said strip is cellulosic.

5. A bibulous strip according to claim 1, wherein said strip further comprises a benzthiazolinone hydrazone diffusibly bound to said strip.

6. A bibulous strip according to claim 1, wherein said aniline is disubstituted on the nitrogen, the second group being alkyl or hydroxyalkyl of from 1 to 3 carbon atoms.

7. A bibulous strip comprising a compound of the formula:

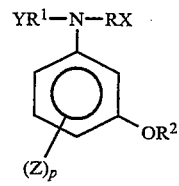

wherein:
R is an alkylene group of from 2 to 6 carbon atoms;
$R^1$ is a bond or an alkylene group of from 1 to 3 carbon atoms;
$R^2$ is hydrogen or an alkyl group of from 1 to 3 carbon atoms;
p is 0 or 1;
Y is hydrogen when $R^1$ is a bond and hydrogen or hydroxyl when $R^1$ is alkylene;
X is a functional group capable of covalently bonding to said bibulous strip; and
Z is a polar group;
with the proviso that the aniline ring may be fused to a second ring to form a bicyclic aromatic compound;

covalently bonded to said bibulous strip through said functional group.

8. A bibulous strip according to claim 7, wherein $R^2$ is methyl.

9. A bibulous strip according to claim 7, wherein X is amino and said bibulous strip has carboxyl groups.

10. A bibulous strip comprising an indamine dye of the formula:

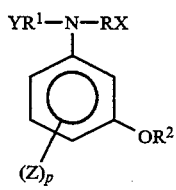

wherein:
R is an alkylene group of from 2 to 6 carbon atoms;
$R^1$ is a bond or an alkylene group of from 1 to 3 carbon atoms;
$R^2$ is hydrogen or an alkyl group of from 1 to 3 carbon atoms;
p is 0 or 1;
Y is hydrogen when $R^1$ is a bond and hydrogen or hydroxyl when $R^1$ is alkylene;
X is a functional group capable of covalently bonding to said bibulous strip; and
Z is a polar group;
with the proviso that the aniline ring may be fused to a second ring to form a bicyclic aromatic compound.

11. A bibulous strip comprising an indamine dye having as the aniline portion a 3-oxy substituted N-(functional group substituted alkyl) aniline.

* * * * *